(12) United States Patent
Tatnell et al.

(10) Patent No.: US 10,590,408 B2
(45) Date of Patent: Mar. 17, 2020

(54) METHOD AND COMPOSITION FOR BIOMOLECULE STABILIZATION

(71) Applicant: GE Healthcare UK Limited, Buckinghamshire (GB)

(72) Inventors: Peter James Tatnell, Cardiff (GB); Elizabeth Mary Ashman, Cardiff (GB)

(73) Assignee: GE Healthcare UK Limited, Buckinghamshire (GB)

( * ) Notice: Subject to any disclaimer, the term of this patent is extended or adjusted under 35 U.S.C. 154(b) by 213 days.

(21) Appl. No.: 15/429,760

(22) Filed: Feb. 10, 2017

(65) Prior Publication Data
US 2017/0240881 A1    Aug. 24, 2017

(30) Foreign Application Priority Data
Feb. 18, 2016 (GB) .................... 1602880.5

(51) Int. Cl.
*C12N 9/96* (2006.01)
*C12N 9/12* (2006.01)
*C12Q 1/686* (2018.01)

(52) U.S. Cl.
CPC ............. *C12N 9/96* (2013.01); *C12N 9/1252* (2013.01); *C12Q 1/686* (2013.01); *C12Y 207/07007* (2013.01)

(58) Field of Classification Search
CPC ....................................................... C12N 9/96
USPC ................................................................ 435/4
See application file for complete search history.

(56) References Cited

U.S. PATENT DOCUMENTS

2014/0113294 A1    4/2014    Horton et al.

FOREIGN PATENT DOCUMENTS

| EP | 2052736 A1 | 4/2009 |
|---|---|---|
| WO | 93/19773 A1 | 10/1993 |
| WO | 02/11540 A1 | 2/2002 |
| WO | 2016/106111 A1 | 6/2016 |
| WO | 2016/106113 A1 | 6/2016 |
| WO | 2016/106129 A1 | 6/2016 |

OTHER PUBLICATIONS

GB Search Report regarding GB Application No. 1602880.5, dated Nov. 7, 2016, 4 pages.

*Primary Examiner* — Jezia Riley
(74) *Attorney, Agent, or Firm* — Eversheds Sutherland (US) LLP

(57) ABSTRACT

The present invention relates to biomolecule stabilization to provide biomolecules, such as sensitive polymerases, in a convenient ready-to-go format. The invention provides a method and composition in which non-ionic surfactant or detergents of the polyoxyethylene cetyl ether family are used, preferably a Brij reagent or a combination of Brij reagents.

9 Claims, 9 Drawing Sheets

| DNA (ng/ul) | Control RTG bead (old) | | | Control RTG bead (new) | | | Brij58 RTG bead (new) | | |
|---|---|---|---|---|---|---|---|---|---|
| | Y1 | Y2 | Y3 | Y1 | Y2 | Y3 | Y1 | Y2 | Y3 |
| 0 | 36.000000 | 36.000000 | 36.000000 | 36.000000 | 36.000000 | 36.000000 | 36.000000 | 36.000000 | 36.000000 |
| 0.01 | 33.564580 | 34.489560 | 34.614970 | 34.563500 | 34.803750 | 33.526650 | 33.553410 | 33.605350 | 33.412820 |
| 0.1 | 31.128220 | 31.241810 | 31.364520 | 30.885930 | 30.611450 | 30.877670 | 31.272710 | 31.157400 | 30.604700 |
| 1 | 28.633650 | 28.325040 | 28.449890 | 28.053880 | 27.392990 | 27.919560 | 28.166920 | 27.918470 | 27.663630 |
| 10 | 25.135260 | 25.333170 | 25.261040 | 24.936250 | 24.695560 | 24.934680 | 25.025450 | 24.817130 | 24.972810 |
| 100 | 22.512520 | 22.501830 | 22.598080 | 21.963280 | 22.093610 | 21.968210 | 22.319150 | 21.937190 | 21.994010 |

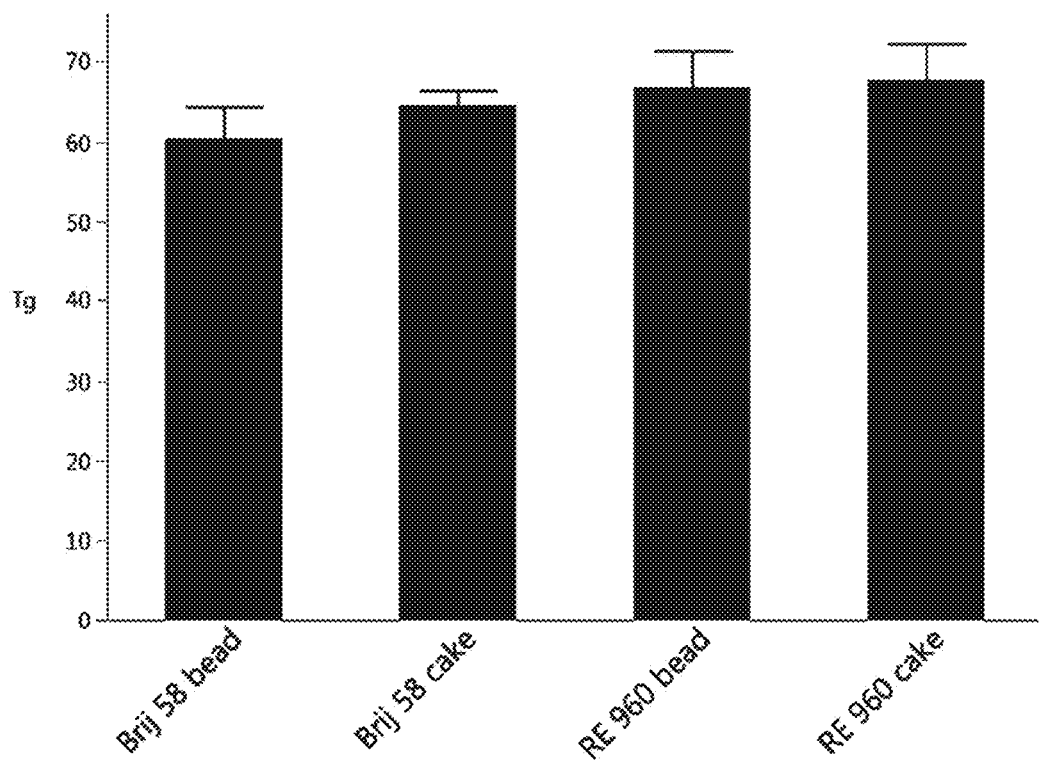

|  | Brij 58 bead | Brij 58 cake | Brij 58 bead | RE 960 bead | RE 960 cake |
|---|---|---|---|---|---|
|  | 56.21 | 65.46 | 56.21 | 69.17 | 72.94 |
|  | 61.10 | 62.39 | 61.10 | 61.51 | 64.89 |
|  | 63.99 | 65.76 | 63.99 | 69.60 | 65.21 |
|  |  |  |  |  |  |
| Mean | 60.43 | 64.54 | 60.43 | 66.76 | 67.68 |
| sd | 3.93 | 1.87 | 3.93 | 4.55 | 4.56 |

| Statistical Comparison | | p-Value |
|---|---|---|
| RE 960 cake | Brij 58 bead | 0.052 |
| RE 960 bead | Brij 58 bead | 0.081 |
| Brij 58 cake | Brij 58 bead | 0.232 |
| RE 960 cake | Brij 58 cake | 0.351 |
| RE 960 bead | Brij 58 cake | 0.504 |
| RE 960 cake | RE 960 bead | 0.779 |

Figure 7: Physical integrity; glass transition temperature (Tg). All datasets were shown to be normally distributed using the Shapiro-Wilk test and shown to be statistically equivalent with each other using the each pair Student's t test ($p > 0.05$).

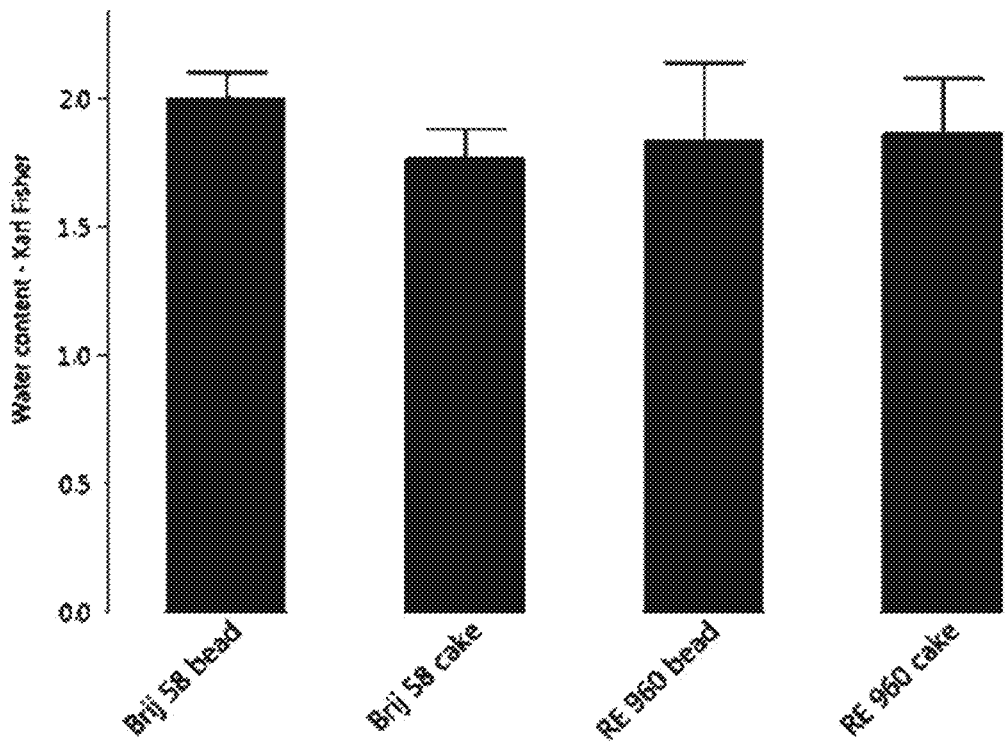

|  | RE 960 bead | RE 960 cake | Brij 58 bead | Brij 58 cake |
|---|---|---|---|---|
|  | 1.9 | 2.1 | 2.1 | 1.7 |
|  | 2.1 | 1.8 | 1.9 | 1.9 |
|  | 1.5 | 1.7 | 2 | 1.7 |
|  |  |  |  |  |
| Mean | 1.83 | 1.87 | 2.00 | 1.77 |
| sd | 0.31 | 0.21 | 0.10 | 0.12 |

| Statistical Comparison |  |  | p-Value |
|---|---|---|---|
| Brij 58 bead | Brij 58 cake |  | 0.116 |
| Brij 58 bead | RE 960 bead |  | 0.337 |
| Brij 58 bead | RE 960 cake |  | 0.438 |
| RE 960 cake | Brij 58 cake |  | 0.643 |
| RE 960 bead | Brij 58 cake |  | 0.822 |
| RE 960 cake | RE 960 bead |  | 0.843 |

Figure 8: Physical integrity; water content, Karl Fisher water analysis. All datasets were tested for normality using the Shapiro-Wilk test and statistically compared with each other using either the each pair Student's t test, or the Wilcoxon Method depending on the distribution. All dataset were shown to be statistically equivalent (p > 0.05).

|  | Brij 58 cake (Original) | Brij 58 (0 weeks) | Brij 58 (6 weeks) | Brij 58 (28 weeks) | Brij 58 (52 weeks) |
|---|---|---|---|---|---|
|  | 65.46 | 65.46 | 66.73 | 62.22 | 59.08 |
|  | 62.39 | 62.39 | 56.03 | 63.1 | 56.95 |
|  | 65.76 | 65.76 | 71.55 | 65.43 | 70.37 |
|  |  |  |  |  |  |
| Mean | 64.54 | 64.54 | 64.77 | 63.58 | 62.13 |
| sd | 1.87 | 1.87 | 7.94 | 1.66 | 7.21 |

| Statistical Comparison |  | p-Value |
|---|---|---|
| Brij 58 (6 weeks) | Brij 58 (52 weeks) | 0.5326 |
| Brij 58 (0 weeks) | Brij 58 (52 weeks) | 0.5689 |
| Brij 58 cake (Original) | Brij 58 (52 weeks) | 0.5689 |
| Brij 58 (28 weeks) | Brij 58 (52 weeks) | 0.7297 |
| Brij 58 (6 weeks) | Brij 58 (28 weeks) | 0.7771 |
| Brij 58 (0 weeks) | Brij 58 (28 weeks) | 0.8199 |
| Brij 58 cake (Original) | Brij 58 (28 weeks) | 0.8199 |
| Brij 58 (6 weeks) | Brij 58 (0 weeks) | 0.9555 |
| Brij 58 (6 weeks) | Brij 58 cake (Original) | 0.9555 |
| Brij 58 cake (Original) | Brij 58 (0 weeks) | 1 |

METHOD AND COMPOSITION FOR BIOMOLECULE STABILIZATION

CROSS-REFERENCE TO RELATED APPLICATIONS

This application claims priority to GB application number 1602880.5, filed Feb. 18, 2016, the entire disclosure of which is hereby incorporated by reference in its entirety.

FIELD OF THE INVENTION

The present invention relates to a method and composition for biomolecule stabilization to provide biomolecules, such as sensitive polymerases, in a convenient ready-to-go format. In both the method and composition non-ionic surfactant or detergents of the polyoxyethylene cetyl ether family are used.

BACKGROUND OF THE INVENTION

Ready-To-Go technology for convenient use of biomolecules is based on a mixture of excipients combined with lyophilisation to provide long-term room temperature stability to biomolecules and reagents including proteins, enzymes etc. The stability is attributed to the fact that the lyophilized biomolecules or proteins exist in an amorphous glassy state that markedly reduces molecular mobility and subsequent reactivity. The glass transition temperature (Tg) for a lyophilized product indicates the temperature at which the glass state begins to transition to a more mobile flexible state, allowing molecular mobility and biomolecule activity to return but with a consequential loss of stability. Knowledge of the Tg value is thus important, as a lyophilized product must be stored below this temperature for long-term stability. Ready-To-Go having Tg values well above room temperature ensure that the products can be shipped and stored without the need for refrigeration. Since the introduction of the first Ready-To-Go product, the technology has demonstrated numerous benefits for the stabilization of a variety of reagents and complex assay mixtures. The technology is suitable for use with sensitive low stability enzymes, antibodies, primers, probes, dyes and other reagents. The physically stable, solid lyophilised reagent provides long term stability at ambient temperature, can be dispensed in flexible formats, and is amenable to downstream manipulation. The compatibility of Ready-To-Go technology with complex mixtures enables the formulation and stabilization of pre-dispensed, single-dose reagents and reaction mixtures. This format can reduce cross-contamination risk and improve data reliability by requiring fewer pipetting steps and less handling overall. Fewer assay steps supports reduced training requirements and simplifies automation of the process.

The temperature stability of Ready-To-Go stabilized materials simplifies and reduces costs for shipping and storage. These materials do not require dry- or wet-ice shipment, which simplifies shipping across countries. Items can be shipped to remote regions or regions with insufficient infrastructure without the concerns or costs associated with temperature-controlled shipments. Once the materials arrive, they can be stored at ambient temperature at the point of use, in the field or lab. Preferably Ready-To-Go products and reagents are heat-sealed under low humidity conditions and stored at ambient temperature in an airtight foil pouch with desiccant.

Taq DNA polymerase Ready-To-Go PCR Beads (GE Healthcare) consist of a pre-formulated, pre-dispensed, freeze-dried PCR reagents mix for single-dose reactions delivering robust and reproducible performance in standard PCR amplifications. The beads and the constituent reagents are room temperature stable and as such offer significant advantages over traditional PCR amplification workflows. A bead is defined as a spherical shape.

The long-term ambient-temperature stable property means that no specialised freezer space is required and therefore less energy is consumed when shipping and storing the product. When being used researchers simply add the template DNA solution and primers of interest and initiate the appropriate thermo-cycle. The bead format reduces the need for multiple pipetting steps and as such minimises the risk of pipetting errors and DNA contamination thereby delivering a system that is associated with more reproducible results. The beads consist of high-quality recombinant Taq DNA polymerase and high-purity reagents. All of these facilitate the delivery of a highly robust and reproducible performance in the majority of downstream applications such as PCR. The use of recombinant Taq DNA polymerase and other high-purity reagents ensures reliable and robust performance in both end point and real-time fluorescence-based PCR amplifications, and ensures the lowest possible levels of contaminating prokaryotic and eukaryotic nucleic acids. An additional advantage is the beads have been verified for use in real-time quantitative PCR workflows.

The Taq DNA polymerase Ready-To-Go PCR Beads (GE Healthcare) are pre-formulated to ensure greater reproducibility between reactions, minimize pipetting steps, and reduce the potential for pipetting errors. The only additional reagents required are water, primers, and template DNA. The beads are provided pre-dispensed into either 0.2 ml or 0.5 ml PCR tubes. The 0.2 ml tubes are also supplied in a 96-well (8×12) plate format that allows individual strips of eight tubes to be easily removed. This flexibility allows use of the entire 96-well plate, strips of eight, or individual 0.2 ml tubes. When reconstituted, each bead contains ~3.5 units of recombinant Taq DNA polymerase, dATP, dCTP, dGTP, dTTP, stabilizers, BSA and reaction buffer. When a bead is reconstituted to a 25 µl final volume, the concentration of each dNTP is 200 µM in 10 mM Tris-HCl (pH 8.0 at room temperature), 50 mM KCl and 1.5 mM $MgCl_2$.

US 2009/0325263 describes Ready-To-Go PCR cakes (Preparation of glassified biological reagents) formulated in a similar manner to Taq DNA polymerase Ready-To-Go PCR Beads. A cake is defined as non-spherical in shape e.g. concial, flat, square etc, the actual shape is determined by the shape of the receptacle into which the mix is dispensed into.

Current Ready-To-Go beads and cakes consist of the anionic detergent Rodafac RE-960 as a means to stabilise the reagents for ambient temperature storage and use at elevated temperatures in procedures such as PCR, which is described in US 20100159528 A1.

A drawback with current Ready-To-Go beads and cakes is that there appears to be a significant amount of electrostatic energy associated with beads and cakes. This is a particular disadvantage especially for beads dispensed into receptacles such as PCR tubes, Eppendorf centrifuge tube, 96-well PCR and flat-bottomed plates etc as the tendency for the beads to "jump" out of the receptacle due to either electrostatic attractive or repulsive forces. It would be desirable to have an improved manufacturing process providing bead/cakes which exhibit reduced attractive and repulsive forces.

SUMMARY OF THE INVENTION

The present invention provides Ready-To-Go formulations with improved properties.

In a first aspect, the invention relates to a method for stabilizing biomolecules, comprising: treating a biomolecule with a lyophilisation mixture comprising non-ionic surfactant(s) or detergent(s) of the polyoxyethylene cetyl ether family; dispensing said mixture into a receptacle; and freeze-drying said mixture.

Preferably the non-ionic surfactant or detergent of the polyoxyethylene cetyl ether family are selected from Brij 52 (Polyoxyethylene-2-cetyl ether; molecular weight: ~330), Brij 56 (Polyoxyethylene-10-cetyl ether; molecular weight: ~683) and/or Brij 58 (Polyoxyethylene-20-cetyl ether; molecular weight: ~112256 & 58; or from any combination thereof.

The mixture preferably also comprises: a collapse temperature modifier selected from dextran, hydroxyethyl starch, Ficoll and gelatin, preferably Ficoll, most preferably Ficoll 70/Ficoll 400; a bulking agent selected from a sugar or sugar alcohol, such as mannitol, lactose, sucrose, trehalose, sorbitol, glucose, raffinose, melezitose, or amino acids, such as arginine, glycine, histidine, leucine; a stabilizing protein, such as bovine serum albumin (BSA); and a buffering agent, preferably Tris HCl. The non-ionic surfactant or detergent is preferably Brij 52, Brij 56 and/or Brij 58, preferably Brij 58.

The method is especially suitable for stabilization of protein, such as enzymes. In one embodiment the method relates to stabilization of nucleic acid polymerase, such as Taq DNA polymerase. The stabilized polymerase may be used for DNA and RNA amplification e.g. PCR, RT-PCR, isothermal amplification. The amplification may be qualitative or quantitative.

The mixture is formed into beads, cakes, conical, flat or square structure depending on the shape of the receptacle into which the composition is dispensed into. A surprising observation was that electrostatic attraction/repulsion was reduced using Brij e.g. beads did not jump out of the containers during manufacture.

In a second aspect, the invention relates to a stabilized biomolecule composition, comprising the biomolecule stabilized in the above lyophilisation mixture. In one embodiment the biomolecule is stabilized in a mixture comprising 1-20% Ficoll, 5-25% Melezitose, 0.1-5% Brij 58, 0.1-10 mg/mL BSA; and 5-50 mM Tris-HCl pH 9.0. Preferably the composition is in a freeze-dried format provided as a kit. The compositions show long term stability as will be shown in the detailed description of the invention below. The composition may also be in liquid format, in which case the essential ingredients are 1-5% Brij 58, 0.1-10 mg/mL BSA; and 5-50 mM Tris-HCl pH 9.0.

In some embodiments, the biomolecule in the composition is a protein, such as an enzyme, for example a nucleic acid polymerase.

In a third aspect, the invention relates to use of the above biomolecule composition in combination with a solid support, preferably a cellulose based matrix or paper, provided with a biological sample, in an assay involving the biological sample and the stabilized biomolecule. Preferably the biological sample comprises nucleic acid and the stabilized biomolecule is a nucleic acid polymerase and the assay is an amplification reaction, such as PCR.

The solid support may comprise: cellulose based paper, woven or non-woven fibrous materials, including man made, or naturally occurring polymer fibres such as an alginate, mineral fibre based materials such as glass fibre materials. The solid supports may be chemically impregnated/coated and optionally non-impregnated/coated. The solid support may be impregnated with chemicals, such as a weak base, a chelating agent, an anionic surfactant, and optionally an anti-oxidant and optionally a chaotrope. The solid supports may also comprise covalently attached chemicals.

All or portions of the solid support may be added to said biomolecule composition, and optionally a sequestrant, preferably cyclidextrin, is added to counteract surfactant inhibition of biomolecule (enzyme) activity or binding of the specific binding partner in the biological sample. Optionally all or portions of the solid support is washed with an aqueous solution prior to addition to the freeze-dried composition In a fourth aspect, the invention relates to a method for amplification of nucleic acid comprising the steps:

i) contacting a solid support with a biological sample containing nucleic acid;

ii) transferring said solid support to a reaction vessel;

iii) incubating said nucleic acid on the solid support with a freeze dried nucleic acid amplification reagent stabilized in a mixture comprising a non-ionic surfactant or detergents of the polyoxyethylene cetyl ether family, optionally in the presence of a cyclodextrin; and iv) amplifying the nucleic acid to produce amplified nucleic acid, preferably by PCR (polymerase chain reaction). The biological sample could be mammalian, eukaryotic or prokaryotic. An example is blood or other body fluids.

More than one sample nucleic acid may be individually detected simultaneously by detecting a specific amplified nucleic acid sequence associated with each sample nucleic acid, wherein the specific nucleic acid sequences are unique oligonucleotide sequences functioning as labels for each sample nucleic acid.

In a fifth aspect, the invention relates to a kit comprising a solid support and freeze-dried reagent composition comprising a nucleic acid polymerase stabilized in non-ionic surfactant or detergents of the polyoxyethylene cetyl ether family for amplifying an oligonucleotide sequence; and a user instruction manual. The kit may further comprise a receptacle suitable for performing a nucleic acid amplification reaction for one or more sequences of interest.

Definitions

Collapse: The point at which the freeze-dried product softens to the extent that it can no longer support its own structure Critical Temperature: During freeze drying, the maximum temperature of the product before its quality degrades by melt-back or collapse Collapse Temperature Modifier: Reagent that transforms or adjusts the collapse critical temperature Transition Glass Temperature: The interval of temperatures where the material goes from a glassy state to a rubbery state due to an increase of water mobility.

Melt-back: The total collapse of a given freeze-dried formulation resulting from the presence of a liquid during the primary drying phase.

Excipient: Natural or synthetic substances formulated alongside the biomolecule or active ingredient for the purpose of long-term stabilization and bulking up freeze-dried formulations including but not limited to; collapse temperature modifiers, bulking agents, stabilizing proteins and buffering agents.

Biomolecule: Any molecule that is present in living organisms, including large macromolecules such as proteins, carbohydrates, lipids, and nucleic acids, as well as small molecules such as primary metabolites, secondary metabolites, and natural products. The may also be synthetic.

BRIEF DESCRIPTION OF THE DRAWINGS

FIG. 7 Comparison of the glass transition temperature of Taq DNA polymerase Ready-To-Go mixtures manufactured in the presence of either Brij 58 or RE-960 in bead or cake formats.

FIG. 8 Comparison of the water content as determined by a Karl Fisher analysis of Taq DNA polymerase Ready-To-Go mixtures manufactured in the presence of either Brij 58 or RE-960 in bead or cake formats.

DETAILED DESCRIPTION OF THE INVENTION

Figure 1:
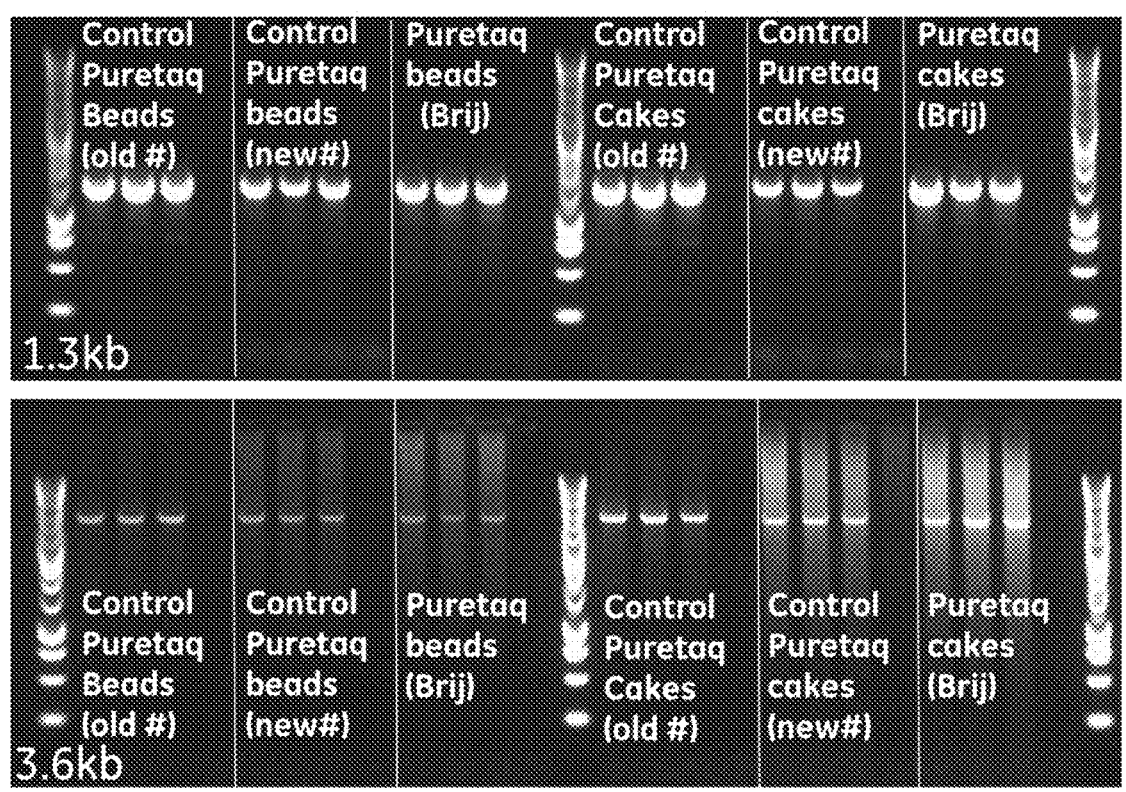
FIG. 1—Genomic DNA Endpoint PCR; Amplification of 1.3 & 3.6 kb amplicons from the human beta-globin gene. The inclusion of Brij 58 into the bulk Taq DNA polymerase Ready-to-Go mix had minimal effect on the amplification efficiency compared to controls consisting of RE-960. This is apparent for both bead and cake formats.

Preparation of Taq DNA Polymerase in Ready-to-go Format

The method of the invention is exemplified by generation of Taq DNA polymerase in Ready-to-Go dry bead and cake formats. Initially, a liquid formulation is generated that is subsequently freeze-dried into the bead and/or cake. Stabilised dry formats facilitate storage and in most instances, easier downstream workflows. The liquid formulation provides for 10 μl aliquot that contains 3.5 U Taq DNA polymerase. The subsequent freeze-dried bead/cake is re-hydrated with 25 μl reaction volume that contains the appropriate oligonucleotide primers and nucleic acid template which can be added either at the time of manufacture or on rehydration by the end user. The final product is a freeze-dried bead or cake reagent that contains all the necessary components to facilitate the PCR amplification of nucleic acids. These reagents are stable at ambient temperatures when stored at low humidity (<20% RH).

Raw Materials

| Material | Supplier | Catalogue Code |
|---|---|---|
| 10 x Cycle Sequencing Buffer | GE Healthcare | 30799 |
| Taq DNA Polymerase | Enzymatics | 29018715 |
| Melezitose | Sigma | M-5375 1198 |
| DNase I RNase free | GE Healthcare | 409636 |
| DNA Polymerization Mix | GE Healthcare | 28406557BS |
| BSA DNase free | Calbiochem | 28954811 |
| Ficoll 70 | GE Healthcare | 17-0310 |
| Ficoll 400 | GE Healthcare | 17-0300 |
| RNase-free DEPC treated water | USB | 70783 |
| Bacterial Chromosomal DNA | Lab | 411576 |
| Tris | USB | 75825 |
| 10M Sodium hydroxide | Fluka | 72068 |
| Potassium chloride | Sigma | P3911 |
| Magnesium chloride | USB | 18641 |
| EGTA | USB | 15703 |
| 10% Brij 58 | Thermo | 28336 |
| 1.0M DTT | Lab | MR014 |
| Ethanol Absolute alcohol | Sigma | 51976 |
| Calcium chloride | Riedel-de Haen | 31307 |
| Hydrochloric Acid | Riedel-de Haen | 30721 |
| 0.2 μm cellulose acetate filter | Nalgene | SFCA 158 |
| Human genomic DNA | Promega | G152A |
| 1.3 kb beta-globin reverse primer | Sigma-Genosys | HA05748544 |
| 1.3 kb beta-globin forward primer | Sigma-Genosys | HA05748543 |
| 3.6 kb beta-globin reverse primer | Sigma-Genosys | HA05748546 |
| 3.6 kb beta-globin forward primer | Sigma-Genosys | HA05748545 |
| Molecular Biology grade water | Sigma | W4502 |
| Exoprostar | GE Healthcare | US77750V |
| Big Dye 3.1 Sequencing kit | Life Technologies | 4336917 |
| Beta-actin qPCR reagent | ABI | 401846 |
| P53 reverse primer | Sigma-Genosys | HA03008180 |
| P53 forward primer | Sigma-Genosys | HA03008179 |
| Bacterial chromosomal DNA | Promega | 411576 |
| Bacterial chromosomal DNA reverse primer | Promega | G2212-2014122 |
| Bacterial chromosomal DNA forward primer | Promega | G2212-2014123 |

Example of Preferred Biomolecule Stabilisation Mixture

| Chemical component | Actual conc | Range |
|---|---|---|
| Ficoll 70 | 9.6% | 1-20% |
| Ficoll 400 | 9.6% | 1-20% |
| Melezitose | 15% | 5-25% |
| Brij 58 | 1% | 0.1-5% |
| Taq DNA polymerase | 3.5 units/bead/cake | 1.0-5 units/bead/cake |
| BSA | 0.6 mg/ml | 0.1-10 mg/ml |
| Tris HCl pH 9.0 | 20 mM | 5-50 mM |
| DNA polymerisation Mix | 0.5 mM | 0.1-10 mM |
| $CaCl_2$ | 0.1 mM | 0.01-5 mM |
| $MgCl_2$ | 2.5 mM | 0.5-5 mM |
| KCl | 50 mM | 10-100 mM |
| DNase | 1 unit/50 units Taq DNA polymerase | 0.5-5 units |

| Chemical component | Actual conc | Range |
|---|---|---|
| EGTA | 10 mM | 1-20 mM |
| DTT | 0.03 mM | 0.01-5 mM |

Methods

Buffer Preparation—

The following buffers were generated using autoclaved DNAse and RNAse-free water following standard laboratory procedure using commercially available reagents. All manufactured buffers were sterilized using 0.2 µM cellulose acetate filters—1.0 M Tris/HCl pH 9, 3.0 M KCl, 1.0 M MgCl$_2$ and 1.0 M CaCl$_2$. Additionally, BSA (10 mg/ml) was prepared and triple filtered using 0.2 µM cellulose acetate filters.

The above solutions were used to generate the Exchange Buffer (20 mM Tris/HCl pH 9.0, 0.1 mM CaCl$_2$, 2.5 mM MgCl$_2$ and 50 mM KCl) supplemented with a concentration range of Brij 58. A control Exchange Buffer was also prepared using the detergent RE-960 as the source of the detergent however in this instance 10 mM Tris/HCl pH 8.0 was used.

Unexpected experimental results (not shown) indicated that Taq DNA polymerase Ready-to-Go beads and cakes manufactured with Brij 58 worked significantly better during PCR reactions at pH 9.0 compared to pH 8.0. Subsequently the "Brij 58 Exchange Buffer" (as described above) contained 20 mM Tris/HCl pH 9.0.

Taq DNA polymerase solution (200 KU/ml) was prepared using Exchange Buffer. DNase I was added to the solution at a ratio of 1 unit DNase per 50 units of Taq DNA polymerase. This was incubated at 37° C. for 22 hours. The DNase was heat inactivated at 75° C. for 15 mM in the presence of 0.03 M DTT and 10 mM EGTA pH 8.0

Preparation of Carbohydrate Excipient Mix—

Ficoll$_{70}$, Ficoll$_{400}$, and Melezitose were mixed until dissolved at 2-8° C. to final concentrations of 9.6%, 9.6% and 15% respectively in the presence of 10× Cycle Sequencing Buffer. The resultant solution was sterilized using a 0.2 µM cellulose acetate filter.

The Taq DNA polymerase Ready-to-Go mix was generated by mixing the following components in a clean sterile polycarbonate bottle to the final concentrations using DNase and RNase-free water—1× Carbohydrate excipient mix, 0.60 mg/ml BSA, 0.5 mM DNA polymerization mix and 0.35 units/µl Taq DNA polymerase. The reagents were stirred for >30 min at 4° C.

Ready-to-go Bead and Cake Preparation—

The freeze-drying procedure involves the following; the bead dropping process dispenses the bulk Taq DNA polymerase Ready-To-Go mix in 10 µl aliquots (containing 3.5 U Taq DNA polymerase) that are immediately frozen by submersion in liquid nitrogen. This can be achieved by using either an automated Bead Dropper device or a standard laboratory pipette. The beads are removed from the liquid nitrogen using a sieve that ensures that beads exhibit a spherical shape with consistent diameter size and weight. Sieving is accomplished at low humidity (<15%). The resultant beads are subjected to drying using a Virtis Freeze Drier set at −46° C., under vacuum for 48 hours.

To generate the Ready-To-Go cakes, bulk Taq DNA polymerase Ready-to-Go mix is treated in a similar way however the mix is dispensed into either the wells of a 96-well PCR or flat bottomed plate etc, immediately frozen and dried under vacuum.

Test of Functional and Physical Properties—

Both the functional and physical properties of the Taq DNA polymerase Ready-To-Go bead and cakes containing the detergent Brij 58 were tested. Functional experimental results focussed on the generation of PCR products amplified from the following sources of DNA:—

[1] Genomic DNA Endpoint PCR: human genomic DNA (1.3 and 3.6 kb amplicons derived from the single copy Beta-globin gene).

[2] Real-time quantitative PCR; using bacterial chromosomal and human genomic DNA as the PCR templates.

[3] Amplicon quality assessment based upon DNA Sequencing: Plasmid DNA (910 bp amplicon derived from p53 gene fragment inserted into pUC-19). The quality and integrity of the resultant PCR products were investigated by performing DNA sequencing as a representative downstream application.

[4] Physical integrity of Ready-To-Go beads and cakes manufactured using either Brij 58 or RE-960.

This test was based upon a close visual inspection of the structure and appearance of beads and cakes manufactured in the presence of either Brij 58 or RE-960. Inspections indicated that no visible differences were observable between either formats irrespective of the detergent used.

[5] Physical integrity of bead or cake; glass transition temperature. The Perkin Elmer Model B016-9321 Differential Scanning calorimeter (DSC) measures the energy changes that occur as a sample is heated, cooled or held isothermally, together with the temperature at which these changes occur. It is used for determining melting points, crystallizations, and measurement of glass transitions and other thermal events. The glass transition temperature (Tg) is a fundamental property of all glass-forming materials, and a significant change in the mechanical properties occurs at this temperature. Below Tg an amorphous material is a glass and above Tg it is defined as being in a more flexible state. Room temperature stability requires the Tg of the product to be higher than the storage temperature.

The DSC was used to measure the Tg of the Taq DNA polymerase Ready-To-Go beads and cakes manufactured using either Brij 58 or RE-960 according to manufacturer's instructions.

[6] Physical integrity of bead or cake; Water content; Karl Fischer (KF) Coulometry. This method is based on the principle that water reacts quantitatively with $I_2$ according to the following equation:

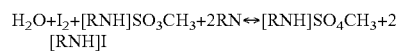

The iodine required for this reaction is generated by electrochemical means in the Coulomat AG Oven. A quantitative relationship between the electric charge and the amount of iodine generated is used for high-precision dispensing of the iodine. The end point of the determination is indicated voltametrically by applying an alternating current to an electrode immersed in the electrolyte. When the free iodine is consumed in the reaction with water the voltage difference across this electrode is drastically reduced and recorded.

As the material to be tested for residual moisture content is a lyophilised solid i.e Taq DNA polymerase Ready-To-Go beads and cakes manufactured using either Brij 58 or RE-960, the water must be driven out of the cake using an oven that is attached to the KF Coulometer. The water is carried into the titration vessel in a stream of dry Nitrogen.
Results An unexpected difference between Brij 58 and RE-960 containing Ready-To-Go beads and cakes was that there appears to be a significant reduction in the amount of electrostatic energy associated with beads and cakes manufactured using Brij 58 compared to those manufactured using RE-960. This is a particular advantage especially for beads dispensed into receptacles such as PCR tubes, Eppendorf centrifuge tube, 96-well PCR and flat-bottomed plates etc as the tendency for the beads to "jump" out of the receptacle due to either electrostatic attractive or repulsive forces is significantly reduced. This represents a major and significant advantage during both the manufacturing process and for the end-user as the bead/cakes exhibit reduced attractive and repulsive forces.

[1] Genomic DNA Endpoint PCR—Amplification of 1.3 & 3.6 kb amplicons from the human beta-globin gene.

Ready-To-Go beads—Amplified DNA yield as determined from a visual inspection of the band intensity of PCR products separated on agarose gel electrophoresis indicated that yields derived from Brij 58 containing Ready-To-Go beads were equivalent to that of controls using RE-960. Band width and intensity were considered equivalent (see FIG. 1).

Ready-To-Go beads cakes—A similar observation was apparent when using Brij 58 containing Ready-To-Go cakes. Band width and intensity were equivalent.

[2] Real-time quantitative PCR; using human genomic DNA and bacterial chromosomal DNA as the PCR templates.

Figure 2:
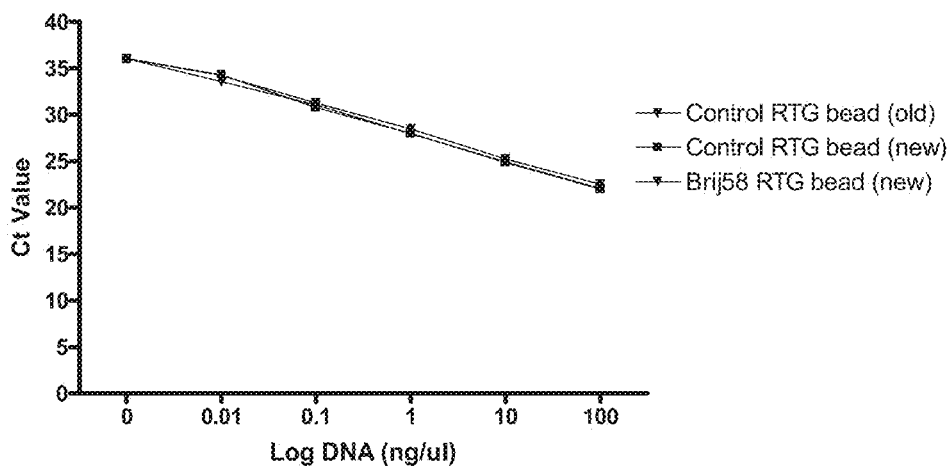
FIG. 2 Eurkaryotic qPCR using Brij 58 containing Ready-To-Go beads. Controls beads were also tested using the detergent RE-960 as the source of the detergent. Results indicated that the inclusion of Brij 58 in the beads had minimal effect on the amplification efficiency compared to RE-960-containing controls.
Figure 3:
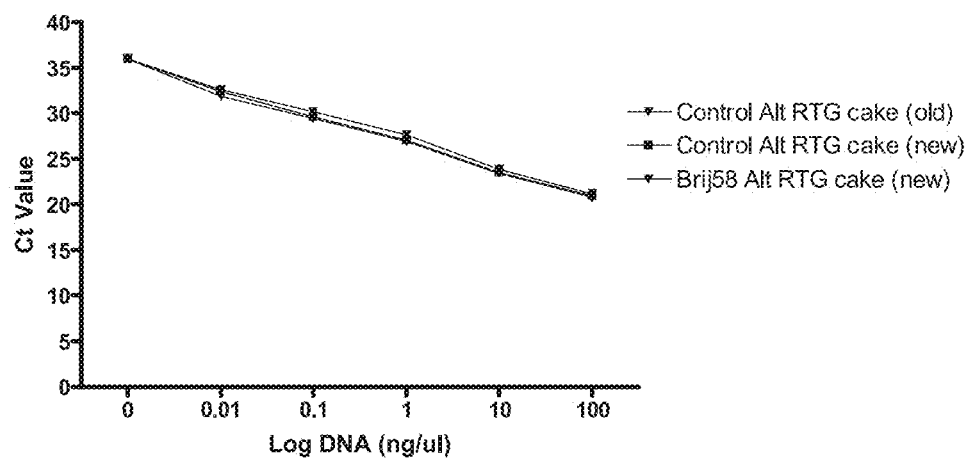
FIG. 3 Eurkaryotic qPCR using Brij 58 containing Ready-To-Go cakes. Controls cakes were also tested using the detergent RE-960 as the source of the detergent. Results indicated that the inclusion of Brij 58 in the cakes had minimal effect on the amplification efficiency compared to RE-960-containing controls.

Eukaryotic DNA—The ability to amplify and quantify a 265 bp amplicon derived from the human Beta Actin gene was used to investigate the efficiency of the Brij 58 containing Taq DNA polymerase Ready-to-Go mixture in both bead and cake formats. Results indicated that the inclusion of Brij 58 had minimal effect on the amplification efficiency compared to RE 960-containing controls (see FIGS. 2 & 3).

Figure 4:
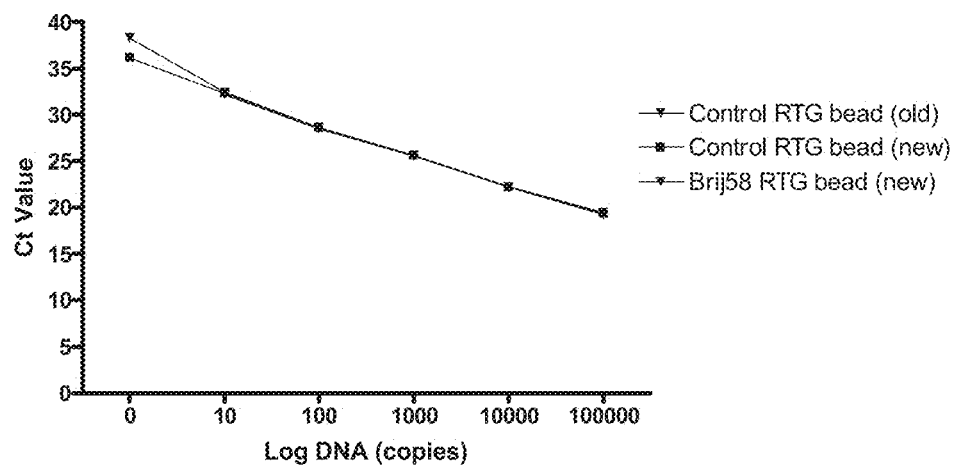
FIG. 4 Prokaryotic qPCR using Brij 58 containing Ready-To-Go beads. Controls beads were also tested using the detergent RE-960 as the source of the detergent. Results indicated that the inclusion of Brij 58 in the beads had minimal effect on the amplification efficiency compared to RE-960-containing controls.
Figure 5:
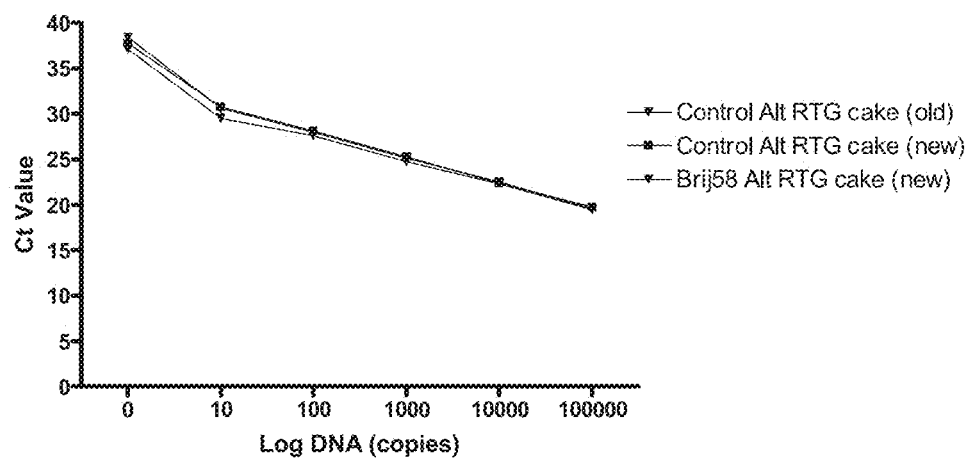
FIG. 5 Prokaryotic qPCR using Brij 58 containing Ready-To-Go cakes. Controls cakes were also tested using the detergent RE-960 as the source of the detergent. Results indicated that the inclusion of Brij 58 in the cakes had minimal effect on the amplification efficiency compared to RE-960-containing controls.

Prokaryotic DNA—The ability to amplify and quantify a 100 bp amplicon derived from bacterial chromosomal DNA was used to investigate the efficiency of the Brij 58 containing Taq DNA polymerase Ready-to-Go mixture in both bead and cake formats. Results indicated that the inclusion of Brij 58 had minimal effect on the amplification efficiency compared to RE-960-containing controls (see FIGS. 4 & 5).

[3] Amplicon quality and integrity assessment based upon DNA Sequencing

Plasmid-based Endpoint PCR was used to generate a 910 bp amplicon derived from p53 gene fragment inserted into the plasmid pUC-19. The quality and integrity of the resultant PCR products were investigated by performing DNA sequencing as a representative downstream application. The DNA sequencing quality metric Phred 20 score were compared for amplicons generated using Ready-To-Go beads and cakes consisting of either Brij 58 or the equivalent control format containing RE-960.

Figure 6:
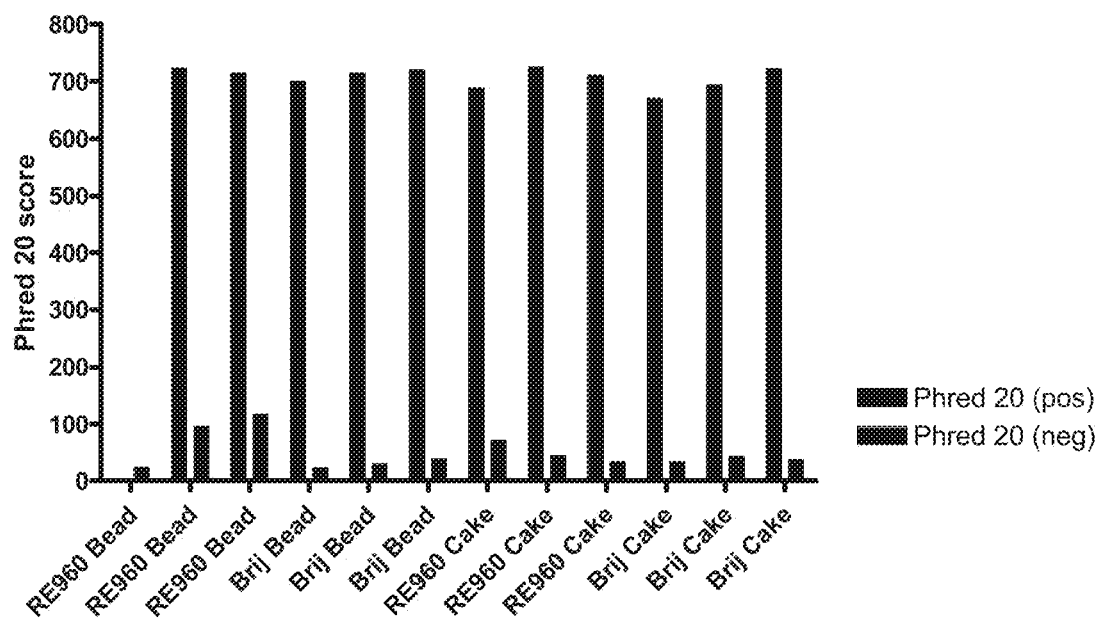
FIG. 6 Amplicon quality assessment based upon DNA Sequencing. Results indicated that equivalent Phred 20 scores were generated using the Taq DNA polymerase Ready-To-Go mixture manufactured in the presence of either Brij 58 or RE-960 and irrespective of bead or cake formats studied.

Results indicated that equivalent Phred 20 scores were generated in the presence of either Brij 58 or RE-960 and irrespective of bead or cake formats (see FIG. 6).

[4] Physical integrity of bead or cake; glass transition temperature.

The glass transition temperature was determined for Taq DNA polymerase Ready-To-Go mixtures manufactured in the presence of either Brij 58 or RE-960 in bead or cake formats. Results indicate (see FIG. 7) that no statistical differences were apparent irrespective of the format i.e. bead versus cake or detergent.

Figure 9:
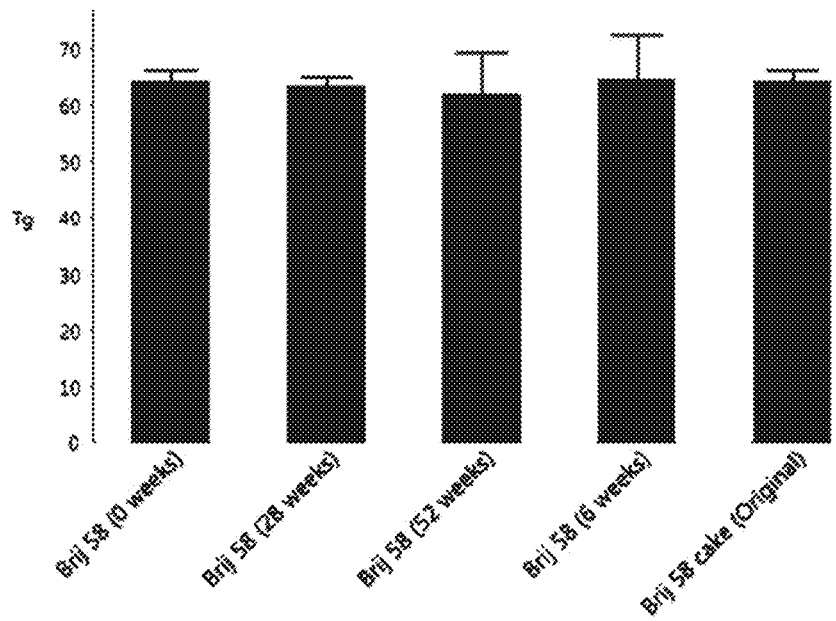
FIG. 9 shows Brij 58 cakes stability data physical integrity; glass transition temperature (Tg). All datasets were shown to be normally distributed using the Shapiro-Wilk test and shown to be statistically equivalent with each other using the each pair Student's t test ($p > 0.05$).

The stability trails in FIG. 9 were performed by storing Brij 58-containing RTG cakes at both real time i.e. 25° C. with a relative humidity of 60% and accelerated conditions i.e. stored at 40° C. with a relative humidity of 75%. The data presented in FIG. 9 was derived from Brij-58 cakes stored for up to one year. The results demonstrate that the manufactured cakes do not deteriorate as measured by the glass transition temperature (Tg).

12 months stability data was performed at accelerated conditions i.e. 40° C. and 75% humidity which equates to 36 months of real time data (25 oc and 60% humidity). This is based upon the Arrenhius equation and an aging factor of (Q10)=2
Reference ASTM F198007

$$\text{Accelerated Aging Time } (AAT) = \frac{\text{Desired Real Time } (RT)}{Q_{10}^{[(T_{AA}-T_{RT})/10]}}$$

[5] Physical integrity of bead or cake; Karl Fisher analysis—water content of beads & cakes The water content of beads & cakes was determined for Taq DNA polymerase Ready-To-Go mixtures manufactured in the presence of either Brij 58 or RE-960 in bead or cake formats. Results indicate (see FIG. 8) that no statistical differences were apparent irrespective of the format i.e. bead versus cake or detergent.

The invention claimed is:

1. A method for stabilizing biomolecules, comprising: treating a biomolecule with a lyophilisation mixture comprising non-ionic surfactant Brij-58 (polyoxyethylene-20-cetyl ether); dispensing said mixture into a receptacle; and freeze-drying said mixture.

2. The method according to claim 1, wherein the mixture also comprises: a collapse temperature modifier selected from dextran, hydroxyethyl starch, Ficoll and gelatin; a bulking agent selected from a sugar or sugar alcohol, or amino acids; a stabilizing protein; and a buffering agent, preferably Tris HCl.

3. The method according to claim 2, for stabilization of protein.

4. The method according to claim 3, for stabilization of nucleic acid polymerase.

5. The method according to claim 4, wherein said mixture is formed into beads, cakes, conical, flat or square structure depending on the shape of the receptacle into which the composition is dispensed into.

6. A stabilized biomolecule composition, comprising a biomolecule stabilized in a mixture comprising non-ionic surfactant Brij 58 (polyoxyethylene-20-cetyl ether).

7. The biomolecule composition according to claim 6, stabilized in a mixture comprising 1-20% Ficoll, 5-25% Melezitose, 0.1-5% Brij 58, 0.1-10 mg/mL BSA; and 5-50 mM Tris-HCl pH 9.0.

8. The biomolecule composition according to claim 7, wherein the stabilized biomolecule is a protein.

9. The biomolecule composition according to claim 8, wherein the stabilized biomolecule is in freeze dried or liquid format.

* * * * *